United States Patent
Chi

(10) Patent No.: US 12,233,262 B2
(45) Date of Patent: Feb. 25, 2025

(54) COSMETIC DEVICE

(71) Applicant: LG ELECTRONICS INC., Seoul (KR)

(72) Inventor: Sanghoon Chi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 208 days.

(21) Appl. No.: 17/914,663

(22) PCT Filed: Oct. 25, 2021

(86) PCT No.: PCT/KR2021/015052
§ 371 (c)(1),
(2) Date: Sep. 26, 2022

(87) PCT Pub. No.: WO2022/244930
PCT Pub. Date: Nov. 24, 2022

(65) Prior Publication Data
US 2023/0338729 A1    Oct. 26, 2023

(30) Foreign Application Priority Data

May 21, 2021   (KR) .......................... 10-2021-0065246

(51) Int. Cl.
*A61N 1/32* (2006.01)
*A61M 37/00* (2006.01)
(Continued)

(52) U.S. Cl.
CPC .......... *A61N 1/328* (2013.01); *A61M 37/0092* (2013.01); *A61N 1/0428* (2013.01);
(Continued)

(58) Field of Classification Search
CPC ........ A61N 1/328; A61N 1/0428; A61N 1/06; A61N 1/28; A61N 1/30; A61N 7/00;
(Continued)

(56) References Cited

U.S. PATENT DOCUMENTS

2004/0024334 A1*   2/2004   Boncompte ............ A61H 9/005
                                                                601/2
2012/0165710 A1*   6/2012   Nichols .............. A61H 23/0263
                                                                601/72
(Continued)

FOREIGN PATENT DOCUMENTS

JP       2014-200499       10/2014
JP       2016-116808        6/2016
(Continued)

OTHER PUBLICATIONS

PCT International Application No. PCT/KR2021/015052, International Search Report dated Mar. 24, 2022, 2 pages.
(Continued)

*Primary Examiner* — Hien N Nguyen
(74) *Attorney, Agent, or Firm* — LEE, HONG, DEGERMAN, KANG & WAIMEY

(57) ABSTRACT

A cosmetic device includes: a body from which a first head portion and a second head portion protrude in directions different from each other; a front assembly disposed on the first head portion; a rear assembly disposed on the second head portion; and an iontophoresis electrode disposed to be spaced apart from the front assembly and the rear assembly on an outer surface of the body. The front assembly includes an inner electrode, an outer electrode disposed outside the inner electrode, and an ultrasonic vibrator disposed on a rear surface of the inner electrode to generate ultrasonic waves. The rear assembly includes a thermoelectric element and a cooling cover cooled by the thermoelectric element.

9 Claims, 12 Drawing Sheets

(51) Int. Cl.
  *A61N 1/04*   (2006.01)
  *A61N 1/06*   (2006.01)
  *A61N 1/28*   (2006.01)
  *A61N 1/30*   (2006.01)
  *A61N 7/00*   (2006.01)

(52) U.S. Cl.
  CPC ................ *A61N 1/06* (2013.01); *A61N 1/28* (2013.01); *A61N 1/30* (2013.01); *A61N 7/00* (2013.01); *A61N 2007/0034* (2013.01)

(58) Field of Classification Search
  CPC .... A61N 2007/0034; A61N 1/40; A61N 5/06; A61N 1/04; A61N 1/32; A61N 1/325; A61N 1/403; A61M 37/0092; A61F 2007/0052; A61F 2007/0075; A61F 2007/0087; A61F 2007/0093; A61F 7/007; A45D 44/00; A45D 2200/202; A45D 2200/207; A61H 23/02; A61H 23/0245
  See application file for complete search history.

(56) References Cited

U.S. PATENT DOCUMENTS

| | | | |
|---|---|---|---|
| 2013/0345661 A1* | 12/2013 | Chang | A61B 17/3207 604/20 |
| 2017/0189227 A1 | 7/2017 | Brunson et al. | |
| 2018/0361437 A1* | 12/2018 | Jansen | B08B 1/32 |
| 2021/0145686 A1 | 5/2021 | Oh et al. | |

FOREIGN PATENT DOCUMENTS

| | | |
|---|---|---|
| JP | 2016-187732 | 11/2016 |
| KR | 10-2001-0086925 | 9/2001 |
| KR | 10-2017-0098577 | 8/2017 |
| KR | 102123668 | 6/2020 |

OTHER PUBLICATIONS

Korean Intellectual Property Office Application No. 10-2021-0065246, Notice of Allowance dated Apr. 21, 2022, 2 pages.

* cited by examiner

[Fig. 1]
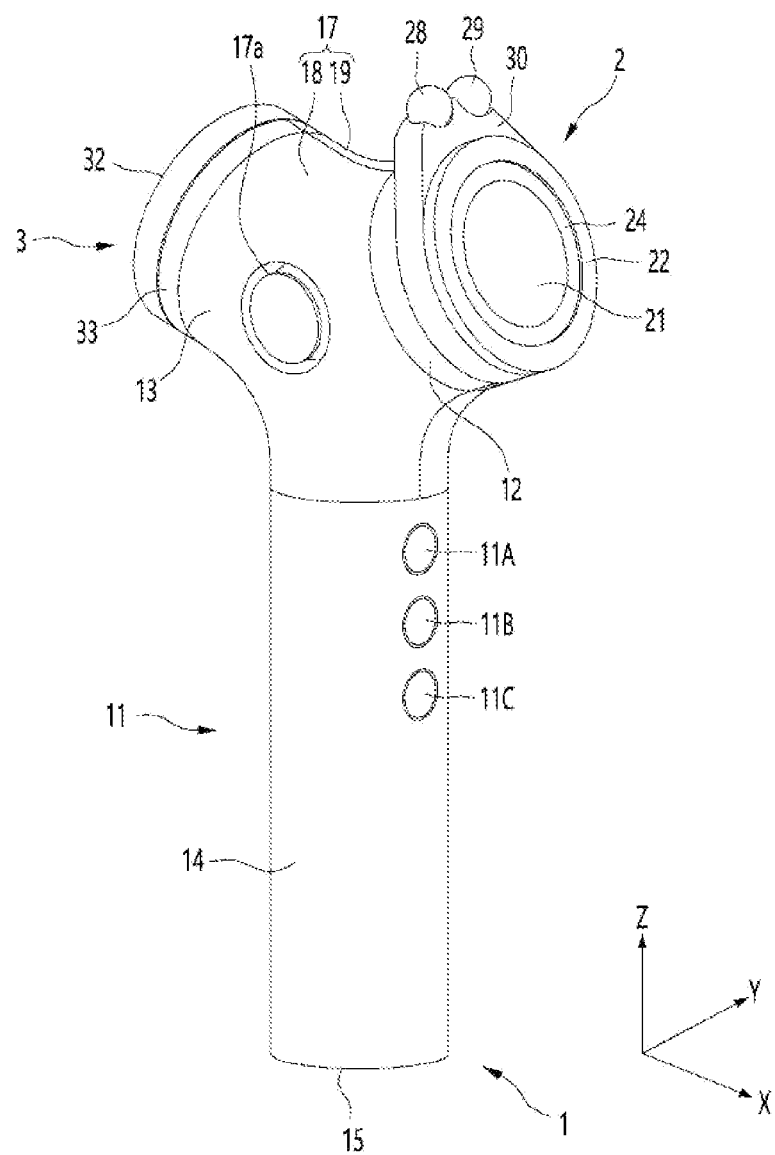

[Fig. 2]
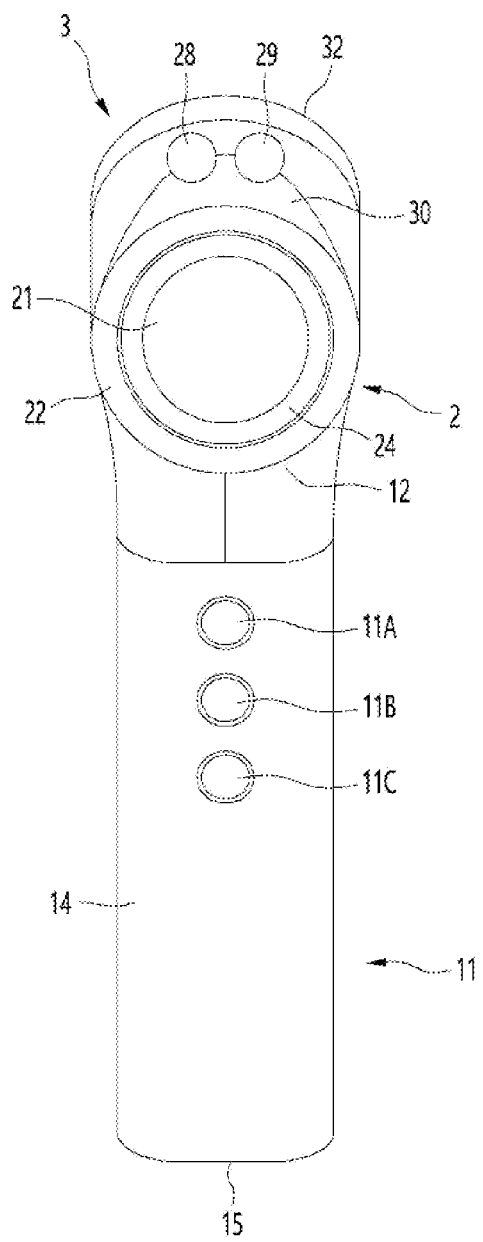

[Fig. 3]
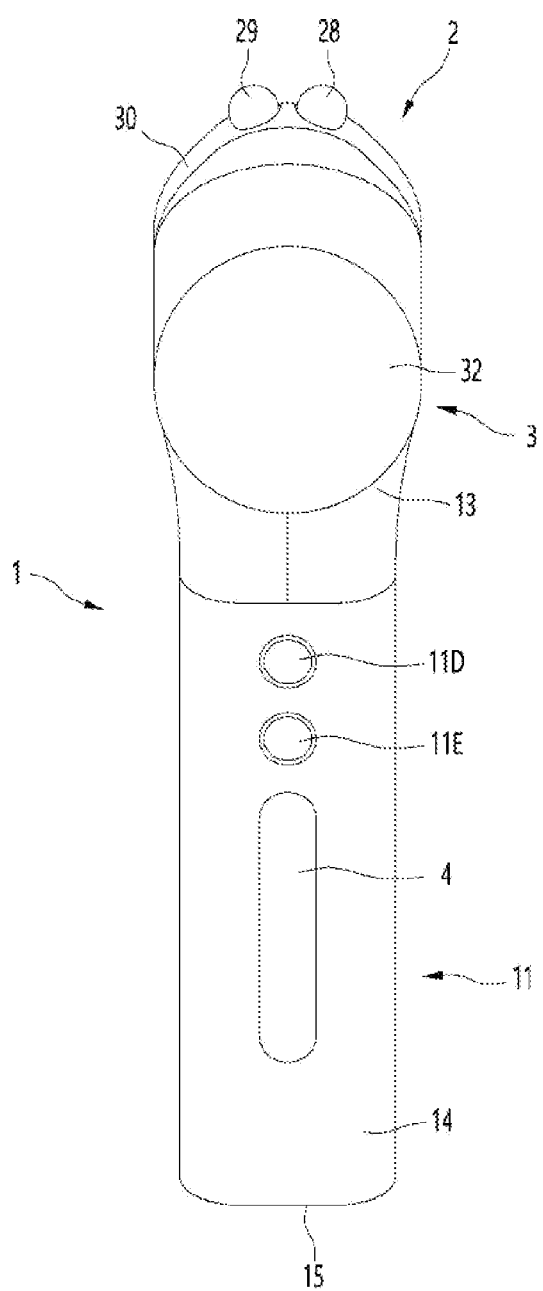

[Fig. 4]
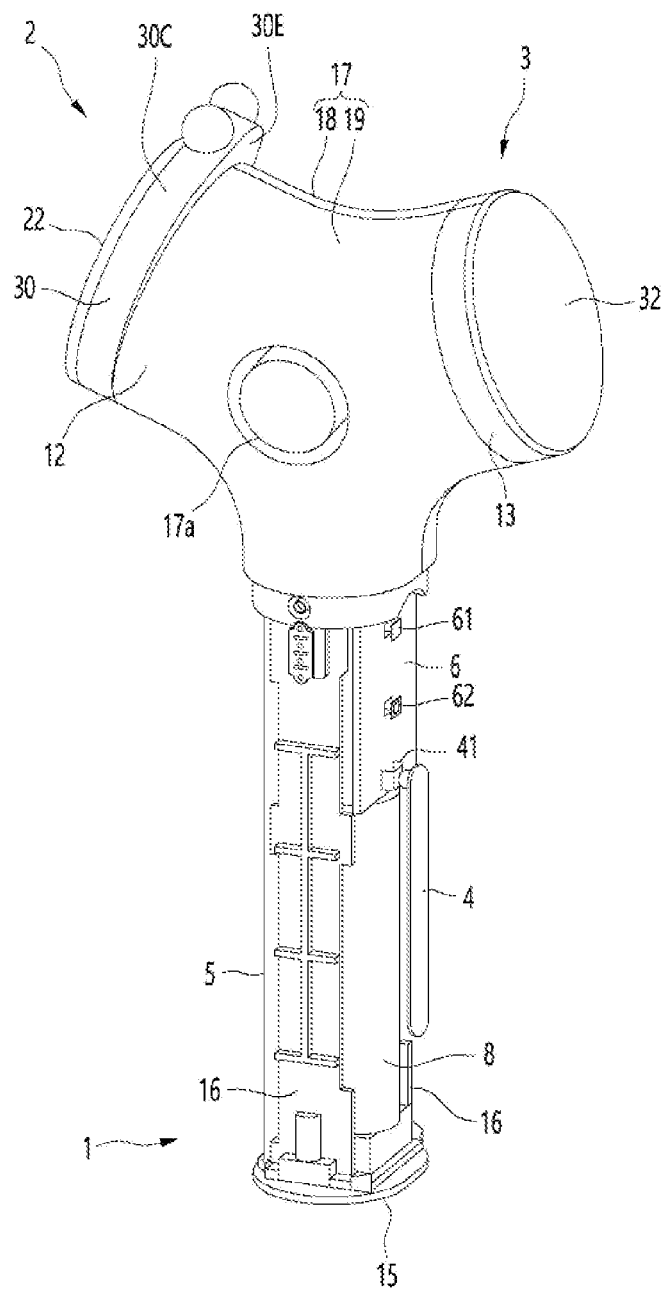

[Fig. 5]
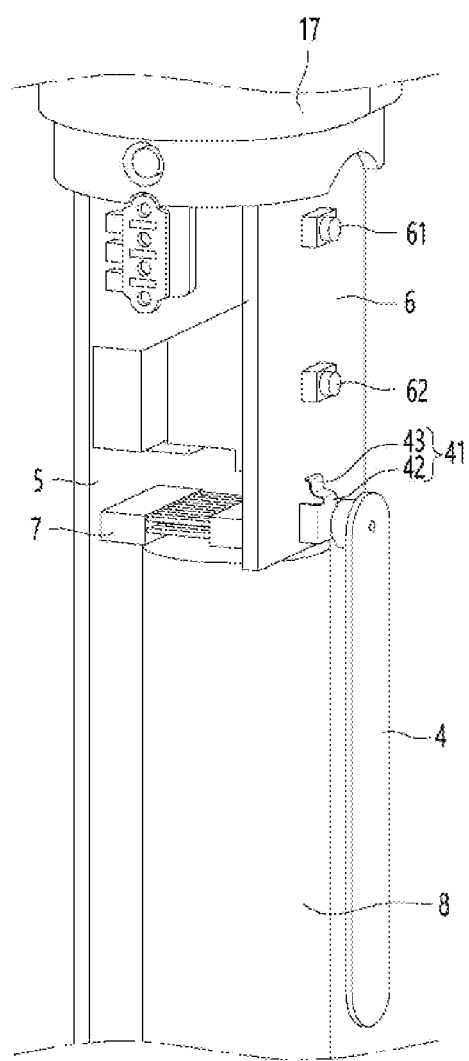

[Fig. 6]
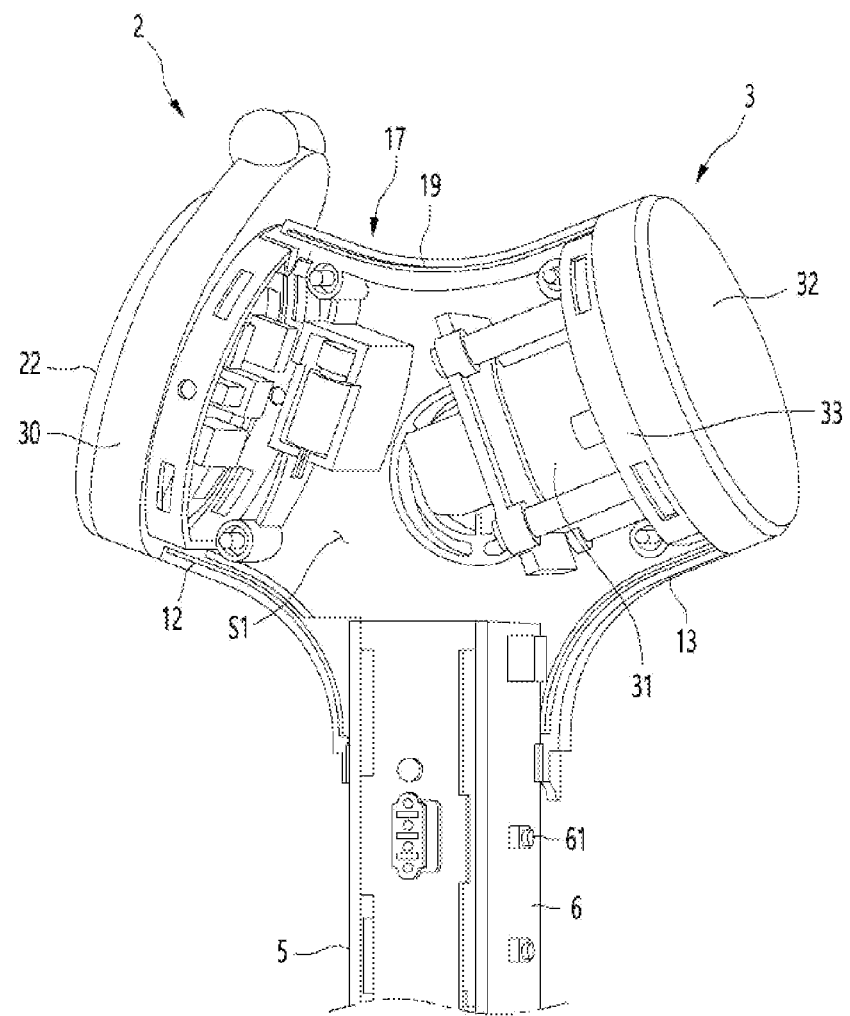

[Fig. 7]
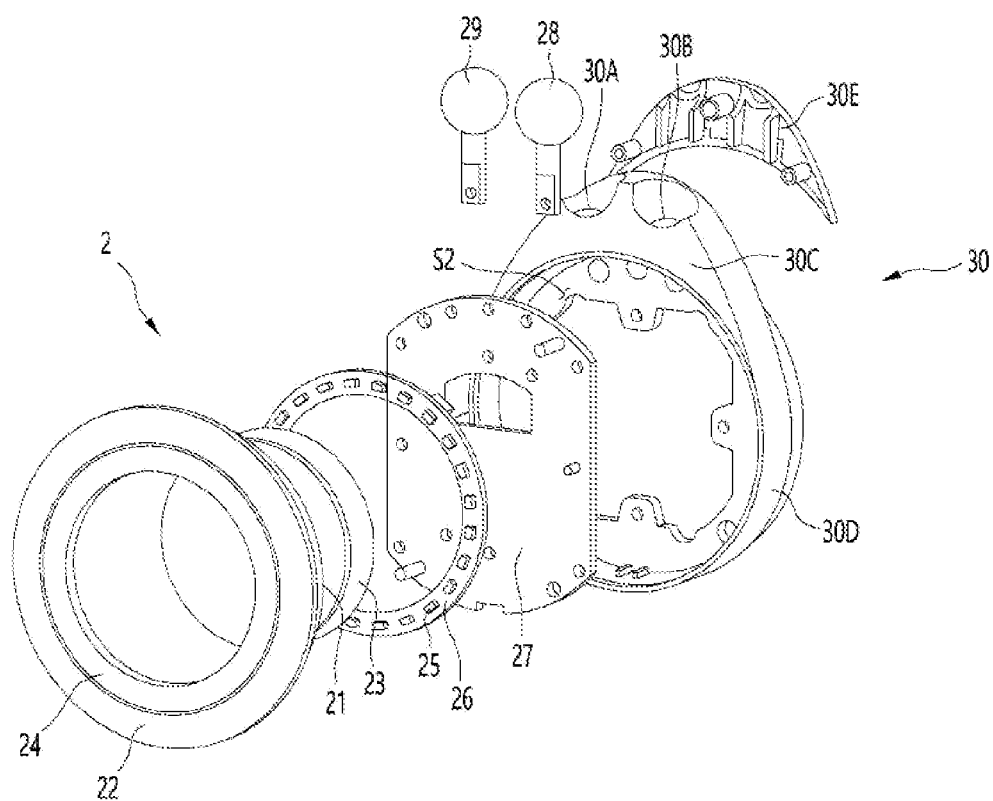

[Fig. 8]
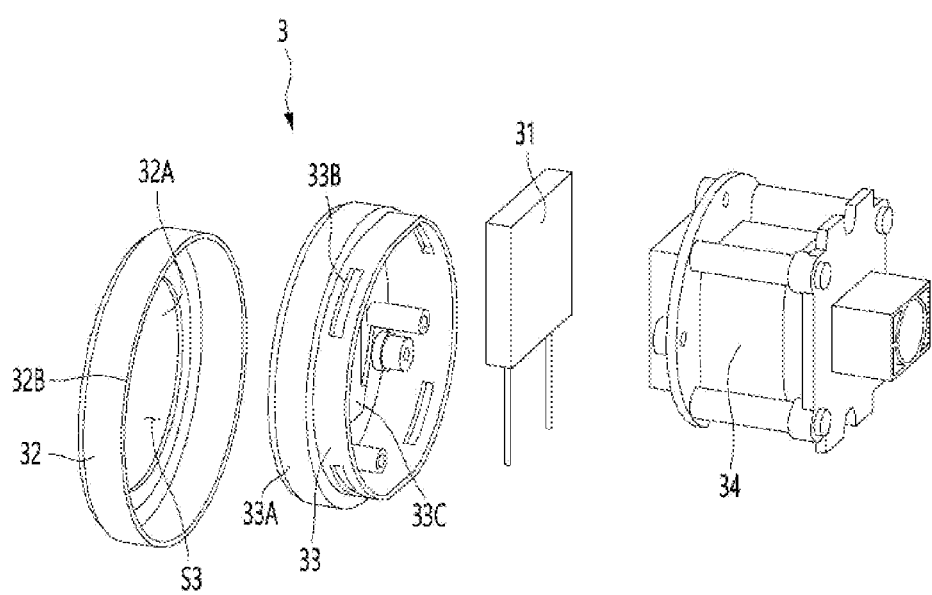

[Fig. 9]
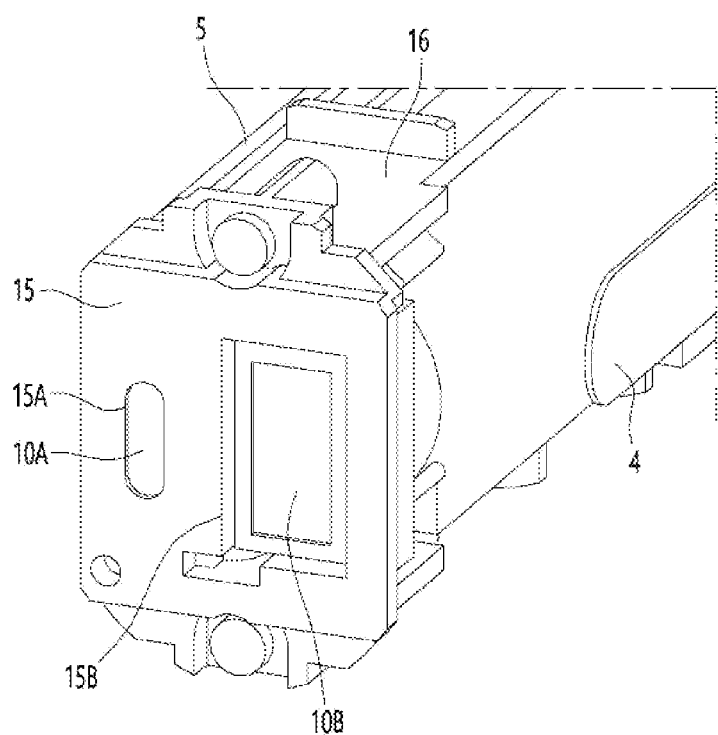

[Fig. 10]
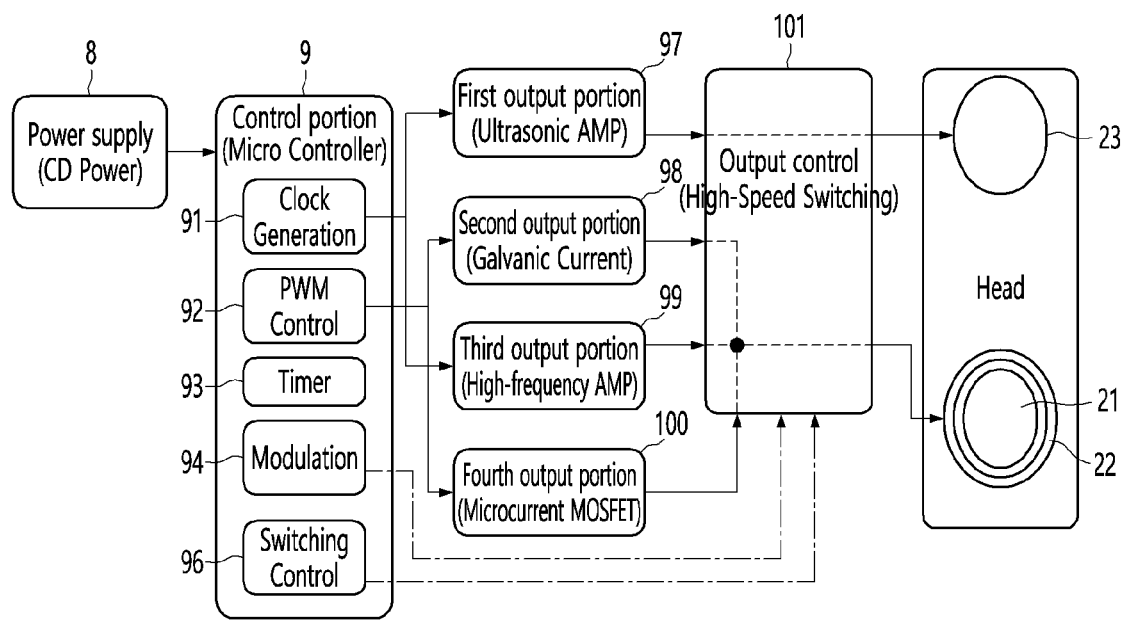

[Fig. 11]
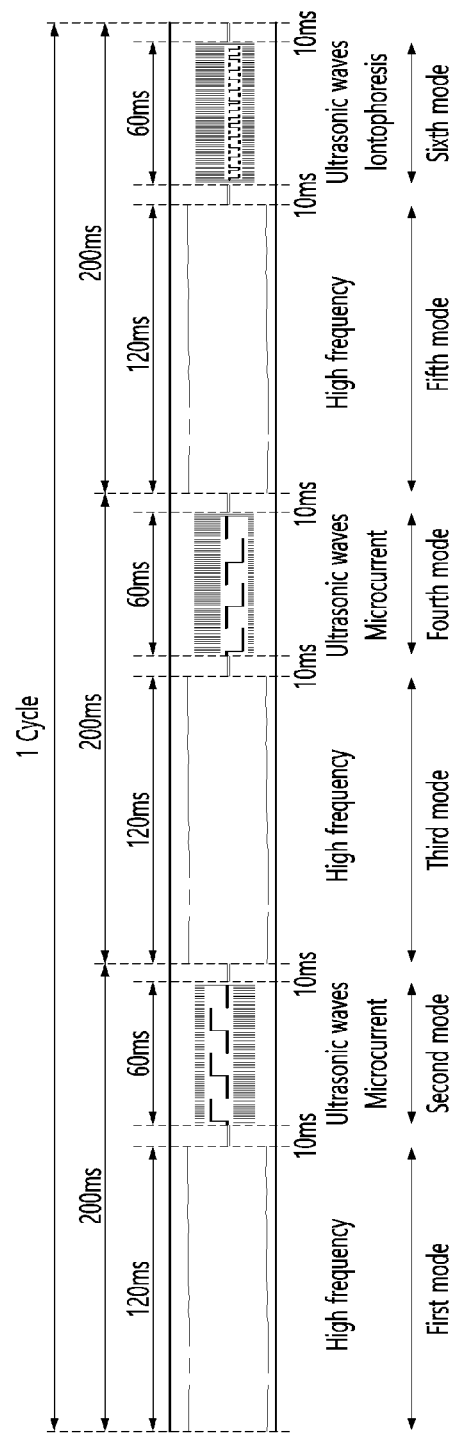

[Fig. 12]
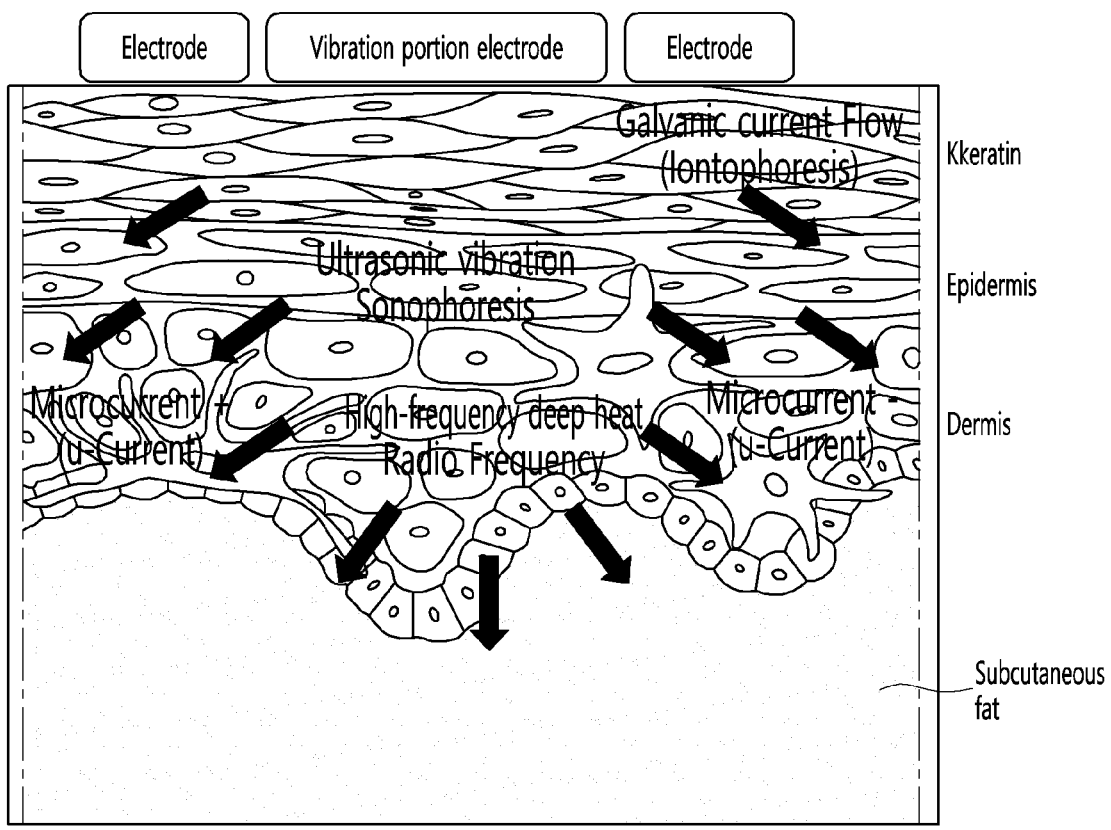

COSMETIC DEVICE

CROSS-REFERENCE TO RELATED APPLICATIONS

This application is the National Stage filing under 35 U.S.C. 371 of International Application No. PCT/KR2021/015052, filed on Oct. 25, 2021, which claims the benefit of earlier filing date and right of priority to Korean Application No. 10-2021-0065246, filed on May 21, 2021, the contents of which are all incorporated by reference herein their entirety.

TECHNICAL FIELD

The present invention relates to a cosmetic device.

BACKGROUND ART

In general, in order to provide nutrition by penetrating effective ingredients of cosmetics deeply into the skin, a cosmetic method of tapping or rubbing the effective ingredients of the cosmetics applied to the skin is being used. Recently, a massage device using a galvanic iontophoresis function or an ultrasonic function or having a hot/cold function is being used.

An example of the message device according to the related art is disclosed in Korean Patent Publication No. 10-2017-0098577 A1 (published on Aug. 30, 2017), which is titled "COMPLEX COSMETIC DEVICE".

The complex cosmetic device includes: a body including a base body having a plurality of ventilation holes, an upper cover coupled to the base body, and a head detachably coupled to the upper cover and in contact with a user's skin to supply ions; a thermoelectric element portion coupled to the body to emit hot or cold heat to the skin through the head; a heat dissipation portion provided in the base body to dissipate heat of the thermoelectric element portion by introducing external air through the plurality of ventilation holes; an ultrasonic wave generator provided in the head to generate ultrasonic waves; and a vibration portion provided on the upper cover to vibrate the head.

DISCLOSURE OF THE INVENTION

Technical Problem

The present invention is to provide a cosmetic device that efficiently supplies a high frequency, microcurrent, ultrasonic waves, and galvanic current in an optimal order by using tree electrodes to increase in absorption rate and penetration depth, thereby improving skin elasticity.

Technical Solution

A cosmetic device according to this embodiment includes: a body from which a first head portion and a second head portion protrude in directions different from each other; a front assembly disposed on the first head portion; a rear assembly disposed on the second head portion; and an iontophoresis electrode disposed to be spaced apart from the front assembly and the rear assembly on an outer surface of the body.

The front assembly includes an inner electrode, an outer electrode disposed outside the inner electrode, and an ultrasonic vibrator disposed on a rear surface of the inner electrode to generate ultrasonic waves.

The rear assembly includes a thermoelectric element and a cooling cover cooled by the thermoelectric element.

The cosmetic device may further include a controller configured to perform a care mode in at least one cycle.

The one cycle includes a first mode, in which a high frequency is output from the outer electrode, a second mode which is performed after the first mode and in which ultrasonic waves are output from the inner electrode, and microcurrent is output from the outer electrode, a third mode which is performed after the second mode and in which a high frequency is output from the outer electrode, a fourth mode which is performed after the third mode and in which ultrasonic waves are output from the inner electrode, and microcurrent having a reverse phase with respect to the second mode is output from the outer electrode, a fifth mode which is performed after the fourth mode and in which a high frequency is output from the outer electrode, and a sixth mode which is performed after the fifth mode and in which ultrasonic waves and galvanic current are output from the inner electrode.

The front assembly may include a window disposed between the inner electrode and the outer electrode, an LED configured to emit light to the window from a rear side of the window, and an LED PCB on which the LED is installed.

The front assembly may further include a head PCB to which each of the inner electrode and the outer electrode is connected.

The front assembly may include a pair of eye care modules connected to the head PCB and spaced apart from each other.

The inner electrode may be configured to output the iontophoresis, the ultrasonic waves, the high frequency, or the microcurrent.

The outer electrode may be configured to output the high frequency or the microcurrent.

The rear assembly may include a rear cover which is configured to support the cooling cover and on which the thermoelectric element is disposed and a heatsink configured to dissipate heat of the thermoelectric element.

The cosmetic device may further include a main PCB on which an input portion configured to input an intensive care mode, a high-frequency generator circuit, and a microcurrent generator circuit are mounted and which is disposed closer to the first head portion of the first head portion and the second head portion in the body.

The cosmetic device may include a sub PCB on which an input portion configured to input a cooling care mode and which is disposed closer to the second head portion of the first head portion and the second head portion in the body.

An ultrasonic generator circuit may be mounted on the sub PCB.

The iontophoresis electrode may be connected to the sub PCB.

Advantageous Effects

According to this embodiment, one device may supply the high frequency, the ultrasonic waves, the microcurrent, and galvanic current by the inner electrode, the outer electrode, the iontophoresis electrode, and the ultrasonic vibrator.

In addition, since the high frequency, the ultrasonic waves, and the microcurrent are supplied to the skin, and then, the galvanic current is supplied, the penetration rate of the cosmetics may be further improved.

In addition, the high frequency and the microcurrent may be quickly and alternately outputted to improve the skin elasticity.

In addition, due to the main PCB and the sub PCB, the body may be more compact than the case, in which the large-sized PCB is embedded in the body, and also, the service may be easy.

In addition, the manipulation for the intensive care mode and the cooling care mode may be easy, the erroneous manipulation of the intensive care mode and the cooling care mode may be minimized to improve the convenience of use.

BRIEF DESCRIPTION OF THE DRAWINGS

FIG. 1 is a perspective view of a cosmetic device according to an embodiment,

FIG. 2 is a front view of the cosmetic device according to an embodiment,

FIG. 3 is a rear view of the cosmetic device according to an embodiment,

FIG. 4 is a view illustrating a state in which a lower housing is separated according to an embodiment, FIG. 5 is a view of a main PCB and a sub PCB according to an embodiment, FIG. 6 is a illustrating a state in which a head housing is separated according to an embodiment, FIG. 7 is an exploded perspective view of a front assembly according to an embodiment, FIG. 8 is an exploded perspective view of a rear assembly according to an embodiment, FIG. 9 is a view of a base according to an embodiment, FIG. 10 is a control block diagram according to an embodiment, FIG. 11 is a flowchart of an intensive care mode according to an embodiment, and FIG. 12 is a view illustrating a depth at which a high frequency, microcurrent, ultrasonic waves, and galvanic current, which are generated by the cosmetic device, are penetrated according to an embodiment.

MODE FOR CARRYING OUT THE INVENTION

Hereinafter, detailed embodiments of the present invention will be described in detail with reference to the accompanying drawings.

FIG. 1 is a perspective view of a cosmetic device according to an embodiment, FIG. 2 is a front view of the cosmetic device according to an embodiment, FIG. 3 is a rear view of the cosmetic device according to an embodiment, FIG. 4 is a view illustrating a state in which a lower housing is separated according to an embodiment, FIG. 5 is a view of a main PCB and a sub PCB according to an embodiment, and FIG. 6 is a illustrating a state in which a head housing is separated according to an embodiment.

As illustrated in FIGS. 1 to 4, a cosmetic device may include a body 1, a front assembly 2, and a rear assembly 3.

The body 1 may include a handle portion 11 and a pair of head portions 12 and 13 protruding upward from the handle portion 11.

The handle portion 11 may be disposed to be elongated in a vertical direction Z. An accommodation space that accommodates a main PCB 5, a sub PCB 6, a battery 8, and the like may be defined in the handle portion 11.

The handle portion 11 may be provided by the lower housing 14, and the accommodation space may be defined in the lower housing 14. The lower housing 14 may be a hollow body that is elongated in the vertical direction Z and has the accommodation space therein.

The handle portion 11 may include a base 15 that defines an outer appearance of a bottom surface of the cosmetic device. The base 15 may be coupled to a lower portion of the lower housing 14. The base 15 may block the accommodation space of the lower housing 14 under the lower housing 14.

The handle portion 11 may further include a PCB mounter 16 that mounts and supports the main PCB 5 and the sub PCB 6.

The PCB mounter 16 may be coupled to the base 15 and may provide a frame of the handle portion 11. The PCB mounter 16 may be disposed inside the lower housing 14.

The PCB mounter 16 may be elongated in the vertical direction Z. A lower portion of the PCB mounter 16 may be coupled to the base 15, and an upper portion of the PCB mounter 16 may be coupled to a head housing 17 to be described later.

A plurality of PCB mounters 16 may be disposed on the base 15.

The plurality of PCB mounters 16 may include a pair of PCB mounters spaced apart from each other in a left and right direction, and the pair of PCB mounters may include a left mounter and a right mounter.

The first head portion 12 and the second head portion 13 constituting the pair of head portions 12 and 13 may protrude in different directions.

The front assembly 2 may be disposed on the first head portion 12, and the first head portion 12 may be a front coupling portion to which the front assembly 2 is coupled.

The first head portion 12 may have an obtuse angle that is inclined with respect to the handle portion 11. The first head portion 12 may be defined as protruding obliquely from an upper portion of the handle portion 11 toward a front upper side. The first head portion 12 may have a hollow shape and may communicate with the handle portion 11 therein.

A rear assembly 3 may be disposed on the second head portion 13, and the second head portion 13 may be a rear coupling portion to which the rear assembly 3 is coupled.

The second head portion 13 may have an obtuse angle that is inclined with respect to each of the handle portion 11 and the first head portion 12. The second head portion 13 may have a hollow shape. The first head portion 13 may be defined as protruding obliquely from an upper portion of the handle portion 11 toward a rear upper side. The second head portion 13 may have a hollow shape and may communicate with the handle portion 11 therein.

The first head portion 12 and the second head portion 13 may be provided by the head housing 17.

The head housing 17 may be provided in an approximately 'Y' shape, and a lower portion of the head housing 17 may constitute the handle portion 11 together with the lower housing 14. An upper portion of the head housing 17 may be divided into two portions to provide the first head portion 12 and the second head portion 13.

The head housing 17 may have a hollow shape. The head housing 17 may be provided as an assembly of a plurality of side housings 18 and 19. The plurality of side head housings may include a left head housing 18 and a right head housing 19.

A space S1 (see FIG. 6) in which a portion of the front assembly 2 and a portion of the rear assembly 3 are accommodated may be defined inside the head housing 17.

A ventilation hole 17a may be defined in the head housing 17 to dissipate heat from a thermoelectric element 31 and a heatsink 34, which will be described later, to the outside. The ventilation holes 17a may be defined in the left head housing 18 and the right head housing 19, respectively.

The front assembly 2 may be disposed on the first head portion 12. A portion of the front assembly 2 may be accommodated in the space S1, and a remaining portion may be exposed to the outside.

The rear assembly 3 may be disposed on the second head portion 13. A portion of the rear assembly 3 may be accommodated in the space S1, and a remaining portion may be exposed to the outside.

The cosmetic device may include an iontophoresis electrode 4.

As illustrated in FIG. 3, the iontophoresis electrode 4 may be disposed on an outer surface of the body 1. The iontophoresis electrode 4 may be disposed on a rear surface of the handle portion 11.

The iontophoresis electrode 4 may be disposed to be spaced apart from the front assembly 2 and the rear assembly 3. The iontophoresis electrode 4 may be disposed in the lower housing 14, and one surface of the iontophoresis electrode 4 may be exposed to the outside in the lower housing 14. When a user holds the handle portion 11, the user's hand may be in contact with the iontophoresis electrode 4.

The iontophoresis electrode 4 may be a plate body elongated in the vertical direction Z.

As illustrated in FIGS. 5 and 6, the iontophoresis electrode 4 may be connected to the main PCB 5 or the server PCB 6 through the connection portion 41.

When the main PCB 5 is greater than the server PCB 6, the iontophoresis electrode 4 may be connected to the sub PCB 6.

As illustrated in FIG. 5, the connection portion 41 may include a connection piece 42 disposed between the sub PCB 6 and the iontophoresis electrode 4.

The connection piece 42 may be disposed to protrude from a rear surface of the sub PCB 6.

The connection portion 41 may include a spring 43 disposed on the connection piece 42. The spring 43 may elastically support the connection piece 42 when pressed against the connection piece 42, and when external force applied to the connection piece 42 is removed, the connection piece 42 may be pressed in a rear direction. An example of the spring 43 may be a leaf spring bent at least once.

As illustrated in FIGS. 4 to 6, the cosmetic device may include the main PCB 5 and the sub PCB 6.

An input portion that inputs an intensive care mode may be disposed on the main PCB 5.

The input portion disposed on the main PCB 5 may include a plurality of switches for the intensive care mode and an eye care mode.

The plurality of switches may be disposed to be spaced apart from each other in a line in the vertical direction on a front surface of the main PCB 5.

The plurality of switches may include a power switch for the intensive care mode and the eye care mode, a mode selection switch for selecting the intensive care mode and the eye care mode, and a level switch for selecting a care level (output intensity).

As illustrated in FIGS. 1 and 2, a power button 11A for switching the power switch, a mode selection button 11B for switching the mode selection switch, and a level button 11C for switching the level switch may be disposed on a front surface of the handle portion 11.

A high-frequency generator circuit and a microcurrent generator circuit may be mounted on the main PCB 5. An iontophoresis generator circuit may be mounted on the main PCB 5.

A power terminal circuit, a battery charging circuit, and a main CPU circuit may be disposed the main PCB 5.

The main PCB 5 may be disposed inside the body 1, in particular, inside the lower housing 14, and a portion of the upper portion of the main PCB 5 may be inserted into the head housing 17.

The main PCB 5 may mainly control the front assembly 2 and be disposed closer to the front assembly 2 of the front assembly 2 and the rear assembly 3.

The main PCB 5 may be disposed closer to the first head portion 12 of the first head portion 12 and the second head portion 13.

An input portion 61 that inputs a cooling care mode may be disposed on the sub PCB 6. The input portion 61 may be a cooling care power switch such as a Tet switch disposed on the rear surface of the sub PCB 6.

The sub PCB 6 may include a cooling care adjustment portion 62 capable of adjusting intensity of the cooling care mode. The cooling care adjustment portion 62 may be a level selection switch, such as a Tet switch, which is disposed on the rear surface of the sub PCB 6 to select a cooling care level (temperature).

As illustrated in FIG. 3, a cooling mode button 11D for switching the cooling care power switch and a level selection button 11E for switching the level selection switch may be disposed on the rear surface of the handle portion 11.

The cooling mode button 11D and the level selection button 11E may be disposed to be spaced apart from the iontophoresis electrode 4 in the vertical direction Z and disposed at a position higher than a height of the iontophoresis electrode 4.

An ultrasonic generator circuit may be mounted on the sub PCB 6.

An iontophoresis connection circuit may be mounted on the sub PCB 6.

The sub PCB 6 may be disposed inside the body 1, in particular, inside the lower housing 14, and a portion of the upper portion of the sub PCB 6 may be inserted into the head housing 17.

The sub PCB 6 may have a size less than that of the main PCB 5. The sub PCB 6 may be arranged in parallel with the main PCB 5.

The sub PCB 6 may be connected to the main PCB 5 and the connector 7.

An example of the connector 7 may be a board-to-board connector.

The connector 7 may be disposed between the main PCB 5 and the sub PCB 6 and may be protected by the main PCB 5 and the sub PCB 6.

The connector 7 may be disposed between the rear surface of the main PCB 5 and the front surface of the sub PCB 6.

The connector 7 may connect a lower portion of the sub PCB 6 to an upper portion or central portion of the main PCB 5.

The sub PCB 6 may control the rear assembly 3 when the user manipulates the input portion 61 or the cooling care adjustment portion 62 and may be disposed closer to the rear assembly of the front assembly 2 and the rear assembly 3.

The sub PCB 6 may be disposed closer to the second head portion 13 of the first head portion 12 and the second head portion 13.

In this embodiment, the power button 11A, the mode selection button 11B, and the level button 11C may be disposed on the front surface of the handle portion 11, and the cooling mode button 11D and the level selection button 11E may be disposed on the rear surface of the handle portion 11. Here, the plurality of buttons 11A, 11B, 11C, 11D, and 11E for the manipulation/input of the cosmetic device may be disposed to be distributed on the front and rear surfaces of the handle portion 11.

When the plurality of buttons 11A, 11B, 11C, 11D, and 11E are disposed to be distributed on the front and rear surfaces of the handle portion 11, the plurality of buttons 11A, 11B, 11C, 11D, and 11E may be spaced apart from each other at a sufficient distance. Also, when any one of the plurality of buttons 11A, 11B, 11C, 11D, and 11E is pressed, pressing of other adjacent buttons may be minimized.

The power button 11A, the mode selection button 11B, and the level button 11C for manipulating the front assembly 2 may be disposed on the front surface of the handle portion 11, and when the cooling mode for manipulating the rear assembly 3 and the level selection button 11E are disposed on the rear surface of the handle portion 11, the user may confuse the buttons when the front assembly 2 or the rear assembly 3 are in contact with his/her face.

The battery 8 may be positioned under the connector 7 and the sub PCB 6 as illustrated in FIG. 5. The battery 8 may be DC power as a power supply, and the same reference numeral will be used for the battery and the power supply.

FIG. 7 is an exploded perspective view of the front assembly according to an embodiment.

The front assembly 2 may be a front head disposed at an upper front side of the cosmetic device.

The front assembly 2 may include an inner electrode 21, an outer electrode 22, and an ultrasonic vibrator 23.

As illustrated in FIGS. 1 and 2, the inner electrode 21 and the outer electrode 22 may be disposed to be exposed to the outside.

The inner electrode 21 may be provided in a circular plate shape as a whole.

The outer electrode 22 may be formed in a ring shape as a whole and may be disposed outside the inner electrode 21. The outer electrode 22 may be disposed to surround the inner electrode 21. An inner diameter of the outer electrode 22 may be greater than a diameter of the inner electrode 21. A ring-shaped gap may be defined between the inner electrode 21 and the outer electrode 22.

When the user brings the inner electrode 21 and the outer electrode 22 to the skin, particularly the face, the inner electrode 21 and the outer electrode 22 may be electrically connected to each other.

The ultrasonic vibrator 23 may be disposed on a rear surface of the inner electrode 21 to generate ultrasonic waves. An example of the ultrasonic vibrator 23 may include a transducer having a size of approximately 5.5 mm.

When the user allows the inner electrode 21 to be in contact with the skin, and the ultrasonic vibrator 21 operates, the ultrasonic vibration may be output through the inner electrode 21.

The inner electrode 21, the outer electrode 22, the ultrasonic vibrator 23, and the iontophoresis electrode 4 (see FIGS. 3 to 5) may output high frequency, microcurrent, ultrasonic waves, and iontophoresis through various combinations.

As an example of the cosmetic device, the inner electrode 21 may output the iontophoresis, the ultrasonic waves, the high frequency, or the microcurrent, and the outer electrode 22 may output the high frequency or the microcurrent.

The iontophoresis may be output by the inner electrode 21 and the iontophoresis electrode 4.

The inner electrode 21 has a negative (−) polarity, and the iontophoresis electrode 4 has a negative (−) polarity opposite to the inner electrode, and negative ions may be output from the inner electrode 21.

The negative ions may output from the inner electrode 21 may push negative charges of cosmetics into the skin, and the cosmetics may be penetrated into the skin more quickly by the negative ions output from the inner electrode 21.

When the ultrasonic vibrator 23 is turned on, the ultrasonic waves and vibrations generated by the ultrasonic vibrator 23 may be output through the inner electrode 21.

The ultrasonic vibration output through the inner electrode 21 may cause cracks in the skin to assist the cosmetics penetration.

The inner electrode 21 and the outer electrode 22 may selectively output a high frequency, positive (+) microcurrent, or negative (−) microcurrent.

The high frequency output from the inner electrode 21 and the outer electrode 22 may generate deep heat in the skin, and the microcurrent output from the inner electrode 21 and the outer electrode 22 may stimulate the skin.

The two electrodes 21 and 22 of the inner electrode 21 and the outer electrode 22 may be electrically connected to each other to form a high-frequency or microcurrent flow.

The front assembly 2 may include a window 24, an LED 25, and an LED PCB 26.

The window 24 may be disposed between the inner electrode 21 and the outer electrode 22. The window 24 may have a ring shape. The window 24 may close a gap between the inner electrode 21 and the outer electrode 22. The window 24 may be disposed to be exposed to the outside.

The LED 25 may emit light to the window 24 from a rear side of the window 24.

The LED 25 may be installed on the LED PCB 26 and be provided in plurality.

The LED PCB 26 may control and support the plurality of LEDs 25. The LED PCB 26 may be provided in a ring shape.

The front assembly 2 may further include a head PCB 27.

Each of the inner electrode 21 and the outer electrode 22 may be electrically connected to the head PCB 27. The LED PCB 26 may be electrically connected to the head PCB 27.

The head PCB 27 may be a kind of junction PCB and may output a high-frequency signal and a microcurrent signal to the outer electrode 22, and also output an LED signal to the LED PCB 26.

In the front assembly 2, the inner electrode 21, the outer electrode 22, the ultrasonic vibrator 23, the window 24, and the LED PCB 25 may be disposed in front of the head PCB 27.

The ultrasonic vibrator 23 may be disposed between a rear surface of the inner electrode 21 and a front surface of the head PCB 27 in a front and rear direction.

The front assembly 2 may further include a pair of eye care modules 28 and 29.

Each of the pair of eye care modules 28 and 29 may be connected to the head PCB 27 and may be spaced apart from each other. The pair of eye care modules 28 and 29 may be in contact with the head PCB 27 so as to be spaced apart from each other in the left and right direction Y.

The pair of eye care modules 28 and 29 may be disposed at a rear upper side of the inner electrode 21 and the outer electrode 22, and each of the pair of eye care modules 28 and 29 may have a size less than that of the inner electrode 21.

The user may allow at least one of the pair of eye care modules 28 and 29 to be closer to a side of an eye area or nose, and the pair of eye care modules 28 and 29 may intensively care for areas to which the inner electrode 21 or the outer electrode 22 do not easy to be approached.

The front assembly 2 may include a front cover 30.

The front cover 30 may be coupled to the first head portion 12, and the front cover 30 may support the inner electrode 21, the outer electrode 22, the ultrasonic vibrator 23, the window 24, the LED PCB. 26, the head PCB 27, and the pair of eye care modules 28 and 29.

The head PCB 27 may be mounted on the front cover 30.

A front space S2 in which the head PCB 27 and the ultrasonic vibrator 23 are accommodated may be defined in the front cover 30. A head PCB coupling portion to which the head PCB 27 is coupled may be disposed on the front cover 30.

Through-portions 30A and 30B through which the pair of eye care modules 28 and 29 pass may be defined in an upper portion of the front cover 30.

The pair of through-portions 30A and 30B may be provided in the same number as the eye care modules 28 and 29. The pair of through-portions 30A and 30B may include a left through-portion, through which the left eye care module 28 passes, and a right through-portion, through which the right eye care module 29 passes.

A protrusion 30C protruding upward may be disposed on the front cover 30, and the pair of through-portions 30A and 30B may be disposed on the protrusion 30C.

The front cover 30 may be provided as a plurality of members, and as illustrated in FIG. 7, a main cover 30D having the front space S2 and the protrusion 30C provided therein and a server cover 30E coupled to a rear surface of the protrusion 30C.

In the intensive care mode, the user may allow the inner electrode 21 and the outer electrode 22 to be in contact with the face.

In the eye intensive care mode, the user may allow the eye care modules 28 and 29 to be in contact with the face.

FIG. 8 is an exploded perspective view of a rear assembly according to an embodiment.

The rear assembly 3 may be a rear head disposed at an upper rear side of the cosmetic device.

The rear assembly 3 may include a thermoelectric element 31 and a cooling cover 32 cooled by the thermoelectric element 31. The rear assembly 3 may include a rear cover 33 and a heatsink 34.

The thermoelectric element 31 may cool the cooling cover 32 in front of the cooling cover 32. A rear surface of the thermoelectric element 31 may be in surface contact with the cooling cover 32.

The cooling cover 32 may be coupled to the rear cover 33 and may be disposed to be exposed to the outside. When the user is in the cooling care mode, the cooling cover 32 may be in contact with the face.

The cooling cover 32 may include a circular plate portion 32A that is in contact with the thermoelectric element 31 and an edge portion 32B that protrudes forward from an edge of the circular plate portion 32A to surround an outer periphery of the rear cover 33.

An insertion space S3 into which an insertion portion 33A of the rear cover 33 is inserted may be defined in the cooling cover 32.

The rear cover 33 may be coupled to the second head portion 12. The thermoelectric element 31 may be disposed on the rear cover 33, and the rear cover 33 may support the cooling cover 33.

The rear cover 33 may include the insertion portion 33A inserted into the insertion space S3 at a rear side thereof. The rear cover 33 may include a coupling portion 33B coupled to the second head portion 13 at a front side thereof. A accommodation portion 33C in which the thermoelectric element 31 is accommodated may be defined in the rear cover 33.

The heatsink 34 may be coupled to the rear cover 33 to dissipate heat from the thermoelectric element 31. The heatsink 34 may be accommodated in the space S1 defined inside the head housing 17.

FIG. 9 is a view of a base according to an embodiment.

The body 1 may be provided with a charging port 10A for charging the battery 8 and a speaker unit 10B for voice guidance when using the cosmetic device.

The charging port 10A and the speaker unit 10B may be disposed inside the handle portion 11. The charging port 10A and the speaker unit 10B may be disposed on the base 15.

A charging hole 15A communicating with the inside of the charging port 10A may be defined in the base 15. A speaker hole 15B surrounding the speaker unit 10B may be defined in the base 15.

FIG. 10 is a control block diagram according to an embodiment.

The cosmetic device may include a controller 9.

The controller 9 may include a control portion, a first output portion 97, a second output portion 98, a third output portion 99, a fourth output portion 100, and an output switching portion 101.

The control portion 91 may be connected to the first output portion 97, the second output portion 98, the third output portion 99, the fourth output portion 100 and the output switching portion 101 by a signal line or a circuit to control the first output portion 97, the second output portion 98, the third output portion 99, the fourth output portion 100, and the output switching portion 101.

The control portion 91 may be a micro controller and include a clock generation 92, a PWM controller 93, a timer 94, a modulation 95, and a switching control 96.

The first output portion 97 may be an ultrasonic generator, for example, may be an ultrasonic AMP. The first output portion 97 may include an ultrasonic generator circuit mounted on the sub PCB 6. The first output portion 97 may output ultrasonic energy (e.g., 350 Khz).

The second output portion 98 may be a galvanic current generator. The second output portion 98 may include an iontophoresis generator circuit mounted on the main PCB 6. The second output portion 98 may include an iontophoresis connection circuit mounted on the sub PCB 6. The second output portion 98 may output a galvanic current (e.g., 1 Khz).

The third output portion 99 may be a high-frequency generator, for example, may be a high-frequency AMP. The third output portion 99 may include a high-frequency generator circuit mounted on the main PCB 5. The third output portion 99 may output AC high-frequency energy (e.g., 1 Mhz).

The fourth output portion 100 may be a micro-current generator, for example, may be a micro-current MOSFET. The fourth output portion 100 may include a microcurrent generator circuit mounted on the main PCB 5. The fourth output portion 100 may output microcurrent (e.g., +50 Hz or −50 Hz).

The output switching portion 101 may control an output by switching outputs of the first to fourth output portions 92, 93, 94, and 95 at a high speed and may switch the output of the first output portion 97 to the ultrasonic vibrator 23.

The output switching portion 101 may control an output by high-speed switching the outputs of the second to fourth output portions 92, 93, 94, and 95 at a high speed so as to be switched into the inner electrode 21 or the outer electrode 22.

FIG. 11 is a flowchart of the intensive care mode according to an embodiment.

The controller 9 may perform the care mode in at least one cycle.

Here, the care mode may be the intensive care mode among the intensive care mode, the eye care mode, and the cooling care mode.

The user may turn on the cosmetic device by manipulating the power button 11A and may select the intensive care mode by manipulating the mode selection button 11B. Then, the user may select a care level (output intensity) of the intensive care mode by manipulating the level button 11C.

One cycle may be provided as a combination of a plurality of modes sequentially performed over time and may be provided as a combination of six modes in total.

The one cycle may be repeated for a period of 600 ms, and three processes including a first process, a second process, and a third process may be sequentially performed for a period of 200 mS.

The first process and the second process may be repeated to output a combination of ultrasonic waves and microcurrent after high-frequency output.

During the first process and the second process, the high frequency and the microcurrent may be rapidly and alternately outputted to improve skin elasticity. After a long time (for example, 3 minutes) after outputting the high frequency, the microcurrent may not be outputted, but may quickly and alternately output the high frequency and the microcurrent within a period of 200 mS.

In the third process, after outputting the high-frequency, a combination of the ultrasonic waves and the iontophoresis may be outputted.

Hereinafter, one cycle will be described in detail as follows.

One cycle may include a first mode, a second mode, a third mode, a fourth mode, a fifth mode, and a sixth mode.

The first mode may be a mode in which the high frequency is output from the inner electrode 21 and the outer electrode 22. In the first mode, the front assembly 2 may output AC high frequency (e.g., 1 MHz) for a period of 120 Ms to generate deep heat.

The second mode may be performed after the first mode. The second mode may start after a period of 10 ms after an end of the first mode.

The second mode may be a mode in which the ultrasonic wave (e.g., 350 KHz) is output from the inner electrode 21, and the microcurrent (e.g., 50 Hz) is output from the inner electrode 21 and the outer electrode 22. In the second mode, DC microcurrent for tight-up may be output for a period of 60 mS, and the ultrasonic vibrator 23 may also output an ultrasonic wave for a period of 60 mS.

The third mode may be performed after the second mode. The third mode may start after a period of 10 ms after an end of the second mode.

The third mode may be a mode in which the high frequency is again output from the inner electrode 21 and the outer electrode 22. In the third mode, the front assembly 2 may output AC high frequency (e.g., 1 MHz) for a period of 120 Ms.

The fourth mode may be performed after the third mode, and the fourth mode may start for a period of 10 ms after an end of the third mode.

The fourth mode may be a mode in which the ultrasonic wave (e.g., 350 KHz) is output from the inner electrode 21 and the microcurrent having reverse phase with respect to the second mode is output from the inner electrode 21 and the outer electrode 22.

In the fourth mode, the microcurrent (e.g., −50 Hz) may be output for a period of 60 mS, and the ultrasonic vibrator 23 may also output the ultrasonic wave for a period of 60 mS.

The fifth mode may be performed after the fourth mode, and the fifth mode may start for a period of 10 ms after an end of the fourth mode.

The fifth mode may be a mode in which the high frequency is again output from the inner electrode 21 and the outer electrode 22. In the fifth mode, the front assembly 2 may output AC high frequency (e.g., 1 MHz) for a period of 120 mS.

The sixth mode may be performed after the fifth mode, and the sixth mode may start for a period of 10 ms after an end of the fourth mode.

The sixth mode may be a mode in which the ultrasonic wave (e.g., 350 KHz) and the galvanic current (1 KHz) are output from the inner electrode 21.

In the sixth mode, the ultrasonic vibrator 23 may output an ultrasonic wave for a period of 60 mS, and the inner electrode 21 may output galvanic current (1 Khz) for a period of 60 mS.

FIG. 12 is a view illustrating a depth at which the high frequency, the microcurrent, the ultrasonic waves, and the galvanic current, which are generated by the cosmetic device, are penetrated according to an embodiment.

When using the cosmetic device, the high-frequency waves may increase in deep heat inside the skin, the ultrasonic vibrations may generate cavitation in the skin (cracks between tissues), the microcurrent reduce the keratin impedance according to the change in polarity and stimulate the skin, and the iontophoresis due to the galvanic current may improve the penetration rate of the negative charging materials.

During the first to fourth modes, the deep heat caused by the high-frequency output may be penetrated into the keratin, epidermis, dermis, and subcutaneous fat, and the vibration caused by the ultrasonic waves may be transmitted to the keratin, epidermis and dermis, and the positive (+) microcurrent and the negative (−) microcurrent may be penetrated into the keratin, the epidermis and the dermis.

During the fifth to sixth modes, the deep heat caused by the high-frequency output may be penetrated into the keratin, epidermis, dermis, and subcutaneous fat, and the vibration caused by the ultrasonic waves may be transmitted to the keratin, epidermis and dermis, and the galvanic current may be penetrated into the keratin and the epidermis.

As described above, when the galvanic current is applied after increasing in deep heat of the skin, generating the cavitation, and stimulating the skin at the high frequency, the ultrasonic waves, and the microcurrent, the penetration rate of the negative charging materials contained in the cosmetics may be improved.

The above-disclosed subject matter is to be considered illustrative, and not restrictive, and the appended claims are intended to cover all such modifications, enhancements, and other embodiments, which fall within the true spirit and scope of the present disclosure.

Thus, the embodiment of the present disclosure is to be considered illustrative, and not restrictive, and the technical spirit of the present disclosure is not limited to the foregoing embodiment.

Therefore, the scope of the present disclosure is defined not by the detailed description of the invention but by the appended claims, and all differences within the scope will be construed as being included in the present disclosure.

What is claimed is:

1. A cosmetic device comprising:
   a body from which a first head portion and a second head portion protrude in directions different from each other;
   a front assembly disposed on the first head portion;
   a rear assembly disposed on the second head portion; and
   an iontophoresis electrode disposed to be spaced apart from the front assembly and the rear assembly on an outer surface of the body,
   wherein the front assembly comprises:
      an inner electrode;
      an outer electrode disposed outside the inner electrode; and
      an ultrasonic vibrator disposed on a rear surface of the inner electrode to generate ultrasonic waves,
   wherein the rear assembly comprises:
      a thermoelectric element; and
      a cooling cover cooled by the thermoelectric element,
   wherein the cosmetic device further comprising a controller configured to perform a care mode in at least one cycle,
   wherein the at least one cycle of the care mode comprises:
      a first mode, in which a high frequency is output from the outer electrode;
      a second mode which is performed after the first mode and in which ultrasonic waves generated from the ultrasonic vibrator are output through the inner electrode, and microcurrent is output from the outer electrode;
      a third mode which is performed after the second mode and in which a high frequency is output from the outer electrode;
      a fourth mode which is performed after the third mode and in which ultrasonic waves generated from the ultrasonic vibrator are output through the inner electrode, and microcurrent having a reverse phase with respect to the second mode is output from the outer electrode;
      a fifth mode which is performed after the fourth mode and in which a high frequency is output from the outer electrode; and
      a sixth mode which is performed after the fifth mode and in which ultrasonic waves generated from the ultrasonic vibrator are output through the inner electrode and galvanic current are output from the inner electrode at the same time.

2. The cosmetic device according to claim 1, wherein the front assembly comprises:
   a window disposed between the inner electrode and the outer electrode;
   a light emitting diode (LED) configured to emit light to the window from a rear side of the window; and
   an LED printed circuit board (PCB) on which the LED is installed.

3. The cosmetic device according to claim 1, wherein the front assembly further comprises a head PCB to which each of the inner electrode and the outer electrode is connected.

4. The cosmetic device according to claim 3, wherein the front assembly comprises a pair of eye care modules connected to the head PCB and spaced apart from each other.

5. The cosmetic device according to claim 1, wherein the outer electrode is configured to output the high frequency or the microcurrent, and
   the inner electrode is configured to output the iontophoresis, the ultrasonic waves, the high frequency, or the microcurrent.

6. The cosmetic device according to claim 1, wherein the rear assembly comprises:
   a rear cover which is configured to support the cooling cover and on which the thermoelectric element is disposed; and
   a heatsink configured to dissipate heat of the thermoelectric element.

7. The cosmetic device according to claim 1, further comprising:
   a main PCB on which an input portion configured to input an intensive care mode, a high-frequency generator circuit, and a microcurrent generator circuit are mounted and which is disposed closer to the first head portion of the first head portion and the second head portion in the body; and
   a sub PCB on which an input portion configured to input a cooling care mode and which is disposed closer to the second head portion of the first head portion and the second head portion in the body.

8. The cosmetic device according to claim 7, wherein an ultrasonic generator circuit is mounted on the sub PCB.

9. The cosmetic device according to claim 7, wherein the iontophoresis electrode is connected to the sub PCB.

* * * * *